United States Patent [19]
Parkinson

[11] 3,992,448
[45] Nov. 16, 1976

[54] CHEMICAL PROCESS FOR THE PREPARATION OF THIURAM MONOSULFIDES

[75] Inventor: Alan R. Parkinson, Cuyahoga Falls, Ohio

[73] Assignee: The Goodyear Tire & Rubber Company, Akron, Ohio

[22] Filed: Jan. 10, 1975

[21] Appl. No.: 540,190

Related U.S. Application Data

[63] Continuation of Ser. No. 257,648, May 30, 1972, abandoned, which is a continuation of Ser. No. 797,353, Jan. 24, 1969, abandoned, which is a continuation of Ser. No. 721,518, April 15, 1968, abandoned, which is a continuation of Ser. No. 461,551, June 4, 1965, abandoned.

[52] U.S. Cl. ............................................. 260/567
[51] Int. Cl.² .................................... C07C 155/10
[58] Field of Search .................................... 260/567

[56] References Cited
UNITED STATES PATENTS
1,682,290  9/1928  Maximoff ........................... 260/567

OTHER PUBLICATIONS
Davis et al. J. Am. Chem. Soc., vol. 86, pp. 440–442 (1964).
Pauling "College Chemistry" pp. 504, 507 and 512 (1964), Freeman and Co.

*Primary Examiner*—Nicholas S. Rizzo
*Assistant Examiner*—D. B. Springer
*Attorney, Agent, or Firm*—F. W. Brunner; H. C. Young, Jr.

[57] ABSTRACT

This invention relates to an improved method of preparing substituted thiuram monosulphides useful as rubber curing agents, etc.

1 Claim, No Drawings

CHEMICAL PROCESS FOR THE PREPARATION OF THIURAM MONOSULFIDES

This is a continuation of application Ser. No. 257,648 filed May 30, 1972, which is a continuation of Ser. No. 797,353 filed Jan. 24, 1969, which is a streamline continuation of Ser. No. 721,518 filed Apr. 15, 1968, which is a streamline continuation of Ser. No. 461,551, filed June 4, 1965 all now abandoned.

BACKGROUND OF THE INVENTION

According to the prior art, substituted thiuram monosulphides can be prepared by reacting a substituted thiuram disulphide in an aqueous or aqueous alcoholic mixture with a salt of hydrocyanic acid which is soluble in the mixture.

The present invention provides an improvement in this process. Thus, I have unexpectedly found that improved yields of thiuram monosulphides are obtained by reacting a thiuram disulphide with a salt of a hydrocyanic acid in the presence of a salt of a dithiocarbamic acid.

It is preferred that the reaction is conducted in a liquid medium in which the hydrocyanic acid salt and the dithiocarbamic acid salt are soluble. Various liquids can be used representative of which are water, a water-soluble alcohol, dioxane, tetrahydrofuran, dimethyl formamide and a mixture of these.

Thiuram disulphides used in the invention have the general formula:

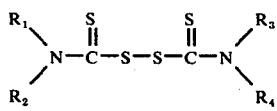

wherein $R_1$, $R_2$, $R_3$, and $R_4$ are individually selected from the group consisting of alkyl, aryl, alkaryl, and aralkyl radicals. Representative of such radicals are alkyl radicals having from 1 to 20 carbon atoms such as methyl, ethyl, propyl, isopropyl, butyl, amyl, hexyl, heptyl and octyl radicals; aryl radicals such as phenyl radicals; alkaryl radicals such as tolyl and xylyl radicals; and aralkyl radicals such as benzyl radicals. Preferably $R_1$ and $R_2$ are the same radicals as $R_3$ and $R_4$ respectively. The two R's on a nitrogen can be joined to form a ring. Such rings may be formed by joining the radicals through a —$CH_2$— radical or through an oxygen, nitrogen, or sulphur atom. Examples of such ring-forming radicals are cycloalkylene, oxydiethylene, thiadiethylene and iminodiethylenes such as methyl iminodiethylene. Some representative examples of the thiuram disulphides are tetramethyl thiuram disulphide, and tetraethyl thiuram disulphide.

The dithiocarbamic acid salts which are used in this invention have the general formula:

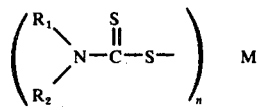

wherein $R_1$ and $R_2$ are preferably the same radicals as $R_1$ and $R_2$ of the substituted thiuram disulphide, M is a radical selected from the group consisting of alkali metals, alkaline earth metals, magnesium, ammonia, and substituted ammonia, and $n$ is an integer which is the same as the valence of M. The various radicals represented by M preferably include the alkali metals such as lithium, sodium, and potassium, rubidium, and cesium; magnesium; the alkaline earth metals such as calcium, strontium, and barium, and radium; ammonium; and substituted ammonium compounds such as dimethyl ammonium, diethyl ammonium and triethyl ammonium.

The salts of hydrocyanic acid used in this invention are cyanides selected from the group consistng of alkali metal cyanides, alkaline earth metal cyanides, magnesium cyanide, ammonium cyanide, and substituted ammonium cyanide. Such cyanides include those of the alkali metals such as lithium, sodium potassium, rubidium, and cesium; magnesium; and of the alkaline earth metals such as calcium, strontium, barium, and radium; ammonia; and substituted ammonias such as dimethyl ammonium, diethyl ammonium, and triethyl ammonium.

The invention can be conveniently carried out by preparing a mixture of a thiuram disulphide in water, alcohol, tetrahydrofuran, dioxane, dimethyl formamide, or a mixture of these. Various alcohols can be used and generally water-soluble alcohols are preferred. Representative examples of such alcohols are methyl alcohol, ethyl alcohol, propyl alcohol butyl alcohol and mixtures of such alcohols. The particle size of the thiuram disulphide can be varied over a wide range. The amount of thiuram disulphide in the mixture can also be varied over a wide range. Generally the mixture will contain from about 1 to about 40 weight per cent of thiuram disulphide.

The reaction is usually initiated under neutral or almost neutral conditions. If desired, the mixture can be made slightly acid according to a litmus paper test by the addition of a small amount of acid. Various acids can be used for this purpose, and generally such acids as sulphuric acid, hydrochloric acid, phosphoric acid, and acetic acid are used.

The dithiocarbamic acid salt is used in the slurry in an amount of up to about 40 mol per cent and generally about 5 to about 20 mol per cent of the mols of the thiuram disulphide.

In carrying out the reaction, the temperature of the mixture is generally adjusted to between about 10° C. to about 150° C. and usually in the range of from about 40° C. to about 70° C. The soluble cyanide is then added to the slurry in an amount up to about 150 mol per cent based on the thiuram disulphide. Usually it is used in an amount of from about 5 to 20 mol per cent based on the thiuram disulphide present.

The following illustrative examples are set forth to further exemplify the objects and advantages of the invention. The parts and percentages are by weight unless otherwise indicated.

EXAMPLE I

A tetramethylthiuram disulphide water slurry was prepared by mixing 160 parts of water with 24 parts of tetramethylthiuram disulphide powder in a flask. The slurry was made acidic to litmus paper by the addition of a few drops of concentrated sulphuric acid. The slurry was then heated to about 55° C. at atmospheric pressure and continuously stirred to maintain a good suspension.

A solution of sodium cyanide was prepared by dissolving 5.4 parts of sodium cyanide in 20 parts of water. Sixty-one parts of the sodium cyanide solution were then slowly added to the tetramethylthiuram disulphide water slurry over a period of 20 minutes. The mixture was continuously stirred at atmospheric pressure at 55° C. during the addition of the sodium cyanide solution and then for an additional 20 minutes. At this time the agitation was discontinued, and the solids were removed from the flask, filtered, and washed with water.

The total crude product yield from the tetramethylthiuram disulphide was 94.0%. This product contained 95.3% tetramethylthiuram monosulphide so that the net yield of tetramethylthiuram monosulphide from tetramethylthiuram disulphide was 89.3%.

EXAMPLE II

A tetramethylthiuram disulphide slurry was prepared, and a reaction was conducted according to the method of Example I with the exception that 0.14 parts of sodium dimethyldithiocarbamate were added to the agitated slurry before the addition of the sodium cyanide solution.

The total crude product yield from the tetramethylthiuram disulphide was 95.5%. This product contained 96.4% tetramethylthiuram monosulphide. Thus, the net yield of tetramethylthiuram monosulphide from tetramethylthiuram disulphide was 92.1%.

EXAMPLE III

A slurry was prepared, and a reaction was conducted according to the method of Example I with the exception that 1.4 parts of sodium dimethyldithiocarbamate were added to the agitated slurry before the addition of the sodium cyanide solution.

The total crude product yield from the tetramethylthiuram disulphide was 98.7%. This product contained 98.2% tetramethylthiuram monosulphide. Thus, the net yield of tetramethylthiuram monosulphide from tetramethylthiuram disulphide was 96.9%.

While certain representative embodiments and details have been shown for the purpose of illustrating this invention it will be apparent to those skilled in the art that various changes and modifications may be made therein without departing from the spirit or scope of the invention.

What is claimed is:

1. In a method of preparing thiuram monosulfide by reacting a water slurry of tetramethyl thiuram disulphide with sodium cyanide, the improvement for providing (1) a product yield of a range of about 95.5 to about 98.7 weight percent and (2) an improved product purity in the range of about 96.4 to about 98.2 weight percent both of said thiuram monosulphide which comprises the sequential steps of first preparing a substantially neutral water slurry of said tetramethyl thiuram disulphide and about 5 to about 20 mole percent, based on said thiuram disulphide, of sodium dimethyl dithiocarbamate, then subsequently slowly mixing with said slurry about 105 to about 120 mole percent, based on said thiuram disulphide, of sodium cyanide and reacting said mixture at a temperature in the range of about 40° C. to about 70° C.

* * * * *